United States Patent
McClurg et al.

(10) Patent No.: US 8,737,564 B2
(45) Date of Patent: May 27, 2014

(54) LOW-BACKGROUND SCATTERING X-RAY DIFFRACTOMETER DEVICES, SYSTEMS, AND METHODS

(75) Inventors: Richard B. McClurg, West Lafayette, IN (US); Paul J. Schields, West Lafayette, IN (US); Rex A. Shipplett, II, Wolcott, IN (US); Gerald Wetli, Goodland, IN (US)

(73) Assignee: Aptuit (West Lafayette), LLC, West Lafayette, IN (US)

( * ) Notice: Subject to any disclaimer, the term of this patent is extended or adjusted under 35 U.S.C. 154(b) by 367 days.

(21) Appl. No.: 13/302,474

(22) Filed: Nov. 22, 2011

(65) Prior Publication Data

US 2012/0155612 A1    Jun. 21, 2012

Related U.S. Application Data

(60) Provisional application No. 61/416,362, filed on Nov. 23, 2010.

(51) Int. Cl.
*G01N 23/20* (2006.01)

(52) U.S. Cl.
CPC ............................. *G01N 23/20008* (2013.01)
USPC .......................................................... 378/80

(58) Field of Classification Search
CPC .......... G01N 23/20025; G01N 23/207; G01N 23/20033; G01N 23/201; G01N 23/20008
USPC ........................................ 378/70–90, 199, 200
See application file for complete search history.

(56) References Cited

U.S. PATENT DOCUMENTS 5,635,138 A    6/1997   Amatucci et al.
6,003,321 A    12/1999  Pinkerton et al.

OTHER PUBLICATIONS

Polentarutti, Maurizio, et al., "A helium-purged beam path to improve soft and softer X-ray data quality," J. Appl. Cryst., 2004, vol. 37, pp. 319-324.
Dewaele, Agnes, et al., "Refinement of the equation of state of tantalum," Physical Review B, 2004, vol. 69, 4 pages.
A.D. Vershinin, et al., "Thermal Expansion of Arsenopyrite in Helium and Air," Inorganic Materials, 2000, vol. 36, No. 6, pp. 551-555.
"Non-ambient X-ray Diffraction and Nanostructure Analysis," brochure, 2009, 14 pp., Anton Paar GmbH, Austria, Europe.
"About—The Gem Dugout," [website page online]. The Gem Dugout, [retrieved Feb. 28, 2012], Retrieved from the Internet: <http://www.thegemdugout.com/general.html>.

*Primary Examiner* — Courtney Thomas
(74) *Attorney, Agent, or Firm* — Jones Robb PLLC (57) ABSTRACT

The disclosure relates to devices for creating a low-background scattering environment proximate to the stage of an x-ray diffractometer, x-ray diffractometer systems comprising the same, and methods for collecting x-ray diffraction data.

28 Claims, 9 Drawing Sheets

LOW-BACKGROUND SCATTERING X-RAY DIFFRACTOMETER DEVICES, SYSTEMS, AND METHODS

This application claims the benefit of U.S. Provisional Patent Application No. 61/416,362, filed Nov. 23, 2010, the entirety of which is incorporated herein by reference.

TECHNICAL FIELD

The disclosure relates to devices for creating a low-background scattering environment proximate to the stage of an x-ray diffractometer, x-ray diffractometer systems comprising the same, and methods for collecting x-ray diffraction data.

BACKGROUND

X-ray diffraction allows for nondestructive analysis of a material, revealing information about the crystal structure, chemical composition, and/or physical properties of the material. The technique measures the scattered intensity of an x-ray beam scattered by a sample as a function of incident and scattered angle and wavelength or energy. Advances in hardware and software have improved the analytical capabilities of x-ray diffraction, providing high precision and accuracy in the measurement of interplanar spacings.

Scattering of the x-ray beam due to air surrounding the sample, however, may in some cases lead to excessive background noise in the patterns and cause reduced quality data and/or difficulty in analyzing the collected data. Thus, there exists a need to create an environment for analysis of a sample by x-ray diffraction wherein scattering by air is reduced. There also exists a need to create such an environment in an automated x-ray diffractometer system.

SUMMARY

The present teachings may solve one or more of the above-mentioned problems and/or may demonstrate one or more of the above-mentioned desirable features. Other features and/or advantages may become apparent from the following description.

In accordance with the detailed description and various exemplary embodiments described herein, the disclosure relates to devices for creating a low-background scattering environment proximate to the stage of an x-ray diffractometer, x-ray diffractometer systems comprising the same, and methods for collecting x-ray diffraction data.

In various exemplary embodiments, the devices for creating a low-background scattering environment proximate to the stage of an x-ray diffractometer may comprise a housing configured to move in an automated manner and a gas flow system in flow communication with the housing and configured to flow air out of the housing to create a low-background scattering environment, wherein the housing is configured to transmit x-ray photons from an x-ray source to an x-ray detector of the x-ray diffractometer. In further exemplary embodiments, the housing may be configured to move in an automated manner to at least a first position and a second position, wherein the housing in the first position is configured to provide access to the x-ray diffractometer stage to load the stage with a sample and wherein the housing in the second position is configured to substantially enclose the stage. In further exemplary embodiments, the gas flow system is configured to flow air out of the housing to create a low-background scattering environment proximate to the stage when the housing is in the second position.

In various other exemplary embodiments, an x-ray diffractometer system may comprise an x-ray diffractometer stage configured to receive a sample to be analyzed, a housing configured to move in an automated manner, a gas flow system in flow communication with the housing and configured to flow air out of the housing to create a low-background scattering environment. In further embodiments, at least a portion of the stage may be configured to move in an automated manner to at least a first position and a second position. In further embodiments, the housing may be configured to move in an automated manner to at least a first position and a second position, wherein the housing in the first position is configured to provide access to the stage to load the stage with a sample and wherein the housing in the second position is configured to substantially enclose the stage and to transmit x-ray photons from an x-ray source to an x-ray detector of the x-ray diffractometer. In additional exemplary embodiments, the gas flow system is configured to flow air out of the housing to create a low-background scattering environment proximate to the stage when the housing is in the second position.

In other exemplary embodiments, a method for collecting x-ray diffraction data from a sample may comprise automatically moving a housing to a first position wherein the housing is configured to provide access to an x-ray diffractometer stage, loading a sample onto the x-ray diffractometer stage, automatically moving the housing to a second position wherein the housing is configured to substantially enclose the x-ray diffractometer stage for creating a low-background scattering environment proximate to the stage, flowing gas out of the housing in the second position to create a low-background scattering environment proximate to the stage, transmitting x-ray photons into the housing, and detecting x-ray photons diffracted from the sample on the stage.

Additional objects and advantages will be set forth in part in the description which follows, and in part will be obvious from the description, or may be learned by practice of the present teachings. At least some of the objects and advantages may be realized and attained by means of the elements and combinations particularly pointed out in the appended claims.

It is to be understood that both the foregoing general description and the following detailed description are exemplary and explanatory only and are not restrictive of the claims; rather, the claims are entitled to their full breadth and scope, including equivalents.

BRIEF DESCRIPTION OF THE DRAWINGS

The accompanying drawings are included to provide a further understanding of the invention, and are incorporated in and constitute a part of this specification. The drawings are not intended to be restrictive of the invention as claimed, but rather are provided to illustrate exemplary embodiments of the present teachings and, together with the description, serve to explain certain principles. In the drawings.

DETAILED DESCRIPTION OF VARIOUS EXEMPLARY EMBODIMENTS

The disclosure contemplates devices and systems for creating a low-background scattering environment in a region proximate to the stage of an x-ray diffractometer and methods for collecting x-ray diffraction data. Devices, systems, and methods of the disclosure may reduce scattering of x-ray beams due to the environment surrounding the sample and may thereby improve the quality of x-ray diffraction data collected from the sample.

The disclosure relates to devices for creating a low-background scattering environment in a region proximate to the stage of an x-ray diffractometer. For purposes of the disclosure, an x-ray diffractometer includes a stage for receiving and holding samples, an x-ray source assembly comprising an x-ray source and optional optical components, an x-ray detector assembly, and a body, which includes, among other things, the instrumentation and casing for the instrumentation. An exemplary x-ray diffractometer for use in various embodiments of the disclosure includes, but is not limited to, PANalytical B.V.'s X'Pert PRO MPD diffractometer.

As used herein, the term "low-background scattering environment," and variations thereof, is intended to mean an environment that reduces the scattering of the x-ray beam as compared to that of an open atmosphere or air environment. Such low-background scattering environments may comprise reduced- or low-pressure environments, for example, those formed by substantially removing air from an enclosure around a sample in an x-ray diffractometer, and/or replacing air with a weakly x-ray scattering gas, such as, for example, helium, hydrogen, neon, methane, ammonia, and/or water vapor. In at least one embodiment, the low-background scattering environment is an environment comprising helium and/or hydrogen. It is within the ability of one ordinarily skilled in the art to compare x-ray diffraction data obtained from a sample in an open or air environment with data obtained from a sample in a low-background scattering environment created by the device, system, or method of the disclosure to determine if scattering is reduced.

One of ordinary skill in the art would understand the meaning of the term "proximate" and that it may, for example, mean the area near or surrounding the stage or a portion thereof.

To create a low-background scattering environment in a region proximate to the stage of an x-ray diffractometer, a housing in accordance with various embodiments of the disclosure may be used to at least substantially enclose (e.g., surround) the stage.

The housing may be configured to move in an automated manner to at least a first position and a second position. When in a first position, the housing can be configured to provide access to the x-ray diffractometer stage, thereby permitting loading (e.g., automated loading) of a sample to the stage. When in a second position, the housing can be configured to substantially enclose the stage. When in the second position, the housing may also be configured to transmit x-ray photons from an x-ray source to an x-ray detector of the x-ray diffractometer.

It is within the ability of one of ordinary skill in the art to select appropriate materials for forming the housing, including consideration of weight, machinability, resistance to deformation, and other such factors. Materials for use in forming the housing include, for example, aluminum, plastics such as poly(methyl)methacrylate, and/or plated steel.

It is within the ability of one of ordinary skill in the art to determine an appropriate size and shape for the housing such that it permits transmission of x-ray photons from an x-ray source assembly to an x-ray detector assembly of the x-ray diffractometer and permits loading of samples when in the first position. The housing may also be configured with a recessed opening to receive the stage. In various exemplary embodiments, a portion of the housing may have a curved outer surface (e.g., a portion of a substantially cylindrical surface) to permit movement of the x-ray source assembly and x-ray detector assembly to rotate around the external surface of the housing. In further embodiments, the housing may be of a size such that the housing does not contact the x-ray source assembly or x-ray detector assembly when in a first position that permits access to the x-ray diffractometer stage for loading of a sample.

To create a low-background scattering environment when the housing is in a second position, the device may in various exemplary embodiments, in accordance with the disclosure, comprise a gas flow system in flow communication with the housing and configured to flow air out of the housing to create a low-background scattering environment proximate to the stage.

The gas flow system may comprise at least one outlet. In various embodiments, the at least one outlet may be configured as a vent or mechanism to permit flow of gas, such as air or helium, from the housing. For example, in at least one embodiment, when the housing is in a closed position, the at least one outlet may be an opening in the housing configured to permit the escape of air that is displaced as a result of gas flowing into the housing, such as providing leaks of gas from one or more locations of the housing. In another embodiment, the outlet may be in flow communication with a vacuum, and the outlet may be a mechanism permitting gas to flow out of the housing to create a reduced- or low-pressure environment in the housing.

The gas flow system may further comprise at least one inlet. In various embodiments, the at least one inlet may permit the flow of gas into the housing. The at least one inlet may be configured to be in flow communication with a gas source to allow gas flow into the housing when the housing is in a closed position. In various embodiments, the introduction of gas into the housing via the at least one inlet may cause the flow of gas out of the at least one outlet.

Figure 1:
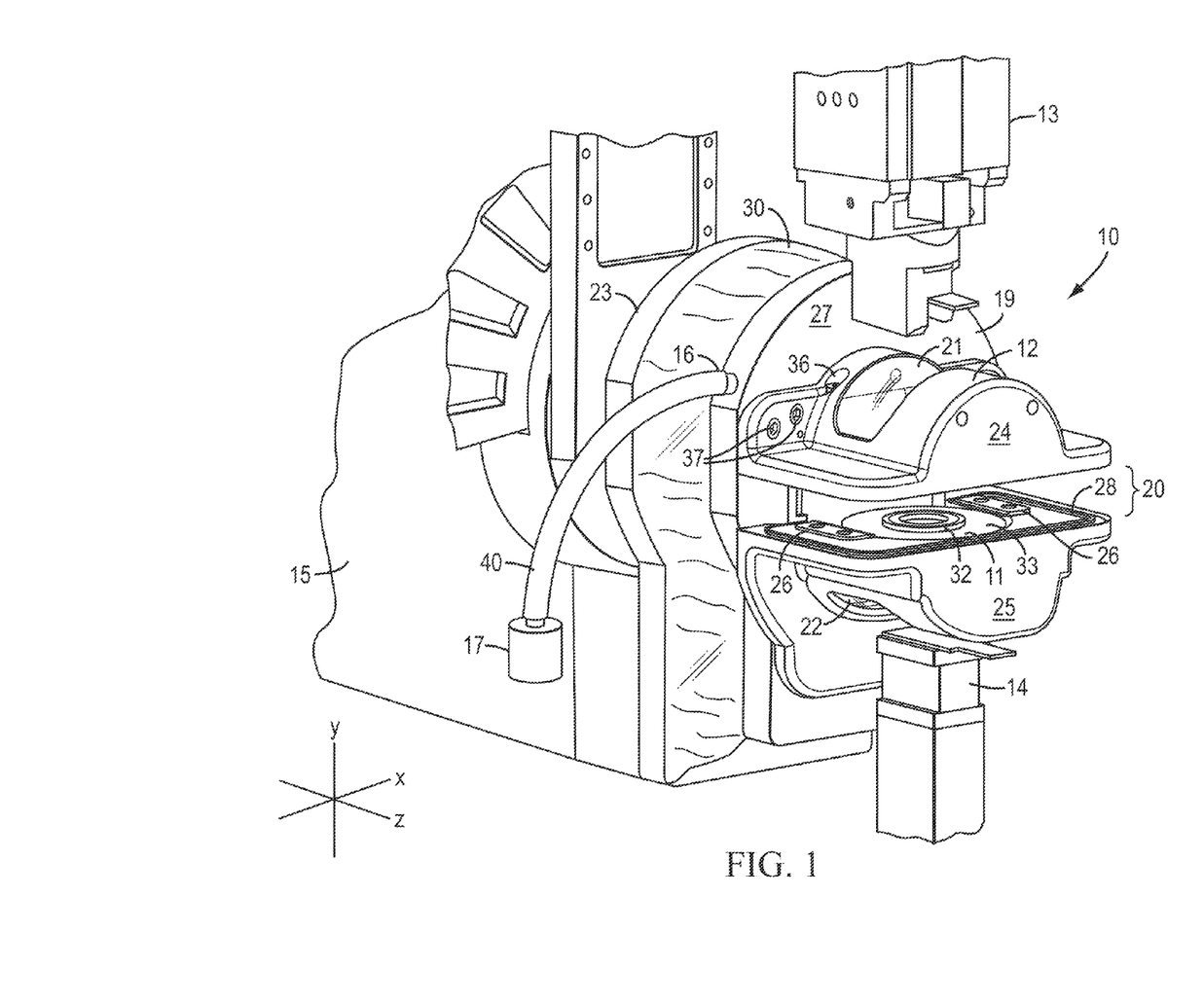
FIG. 1 is a partial perspective view of an exemplary embodiment of an x-ray diffractometer system including a device for creating a low-background scattering environment, wherein the device is in an open position.

With reference to FIG. 1, an exemplary embodiment of an x-ray diffractometer system 10 configured to receive a sample to be analyzed in a low-background scattering environment in accordance with the disclosure is illustrated. The x-ray diffractometer system 10 comprises an x-ray diffractometer stage 11, which may have various configurations with which those having ordinary skill in the art are familiar, and a device 19 for creating a low-background scattering environment in a region proximate to the stage 11 of an x-ray diffractometer, for example, in a region of the stage 11 that is generally disposed between an x-ray source assembly 13 and an x-ray detector assembly 14. It is noted that some elements of the x-ray diffractometer are not illustrated in the figures for purposes of simplicity.

At least a portion of the stage 11 may be configured to move in an automated manner to at least a first position and a second position. For example, a portion of the stage 11, such as the sample-holding surface 33, may be in a first position for loading a sample, as depicted in FIG. 1, and in a second position for analysis of the sample (not shown), whereas the stage base 39 (shown in FIG. 7) may remain stationary. In the embodiment of FIG. 1, a portion of the stage 11, the sample-holding surface 33, moves in the y-direction shown in FIG. 1 from a lower or loading position (in the −y direction) to an upper or analysis position (in the +y direction) in the orientation of the system in FIG. 1.

As illustrated in the exemplary embodiment of FIG. 1, the device 19 comprises a housing 12 that may be configured to move in an automated manner to at least two positions. That is, the housing 12 may move to an open position, depicted in FIG. 1, wherein the housing 12 provides access to the stage 11 to load the stage with a sample (as will also be described in further detail below with reference to FIG. 2), and a closed position, wherein the housing 12 substantially encloses the stage 11 to permit transmission of x-ray photons from the x-ray source assembly 13 to the x-ray detector assembly 14 (as will be described in further detail below with reference to FIG. 3).

The device 19 further comprises a gas flow system 40. In various embodiments, the gas flow system 40 may comprise at least one inlet 16 configured to be in flow communication with a gas source 17 and to allow flow into the housing 12 when the housing 12 is in the closed position. In various embodiments, the gas flow system can include more than one inlet. For example, the gas flow system 40 may comprise two inlets, as will be described in further detail below with reference to FIGS. 5 and 6. In various embodiments, the gas flow system 40 may comprise at least one outlet (not shown) configured to flow gas out of the housing 12 when the housing 12 is in the closed position. As with the inlets, the gas flow system can include more than one outlet in various exemplary embodiments.

In various exemplary embodiments, the housing 12 may be configured to move based on movement of a component of the x-ray diffractometer 15. For example, at least a portion of the housing 12 may be coupled or secured to the x-ray diffractometer body 23 and/or the stage 11, either of which may comprise a portion configured to move automatically. In at least one embodiment, the housing 12 may be secured to the stage 11. In a further embodiment, at least a portion of the housing 12 may be secured to a portion of the stage 11 that is configured to move automatically. It is within the ability of one of ordinary skill in the art to determine appropriate coupling configurations and securing mechanisms to couple or secure the housing 12 to the stage 11. For example, in various embodiments, a portion of the housing 12, such as the second housing portion 25, may be secured to the stage 11 via shims 26 coupled to a surface of the housing 12 and configured to rest on a portion of the stage 11, such as the sample-holding surface 33. In various exemplary embodiments, the device 19 may also comprise a backplate 27, which may be employed for use in coupling the housing 12 to the x-ray diffractometer 15. Further details relating to exemplary coupling configurations are discussed below.

Referring now to FIGS. 2-6, additional aspects and embodiments of the device 19 will be discussed.

Figure 2:
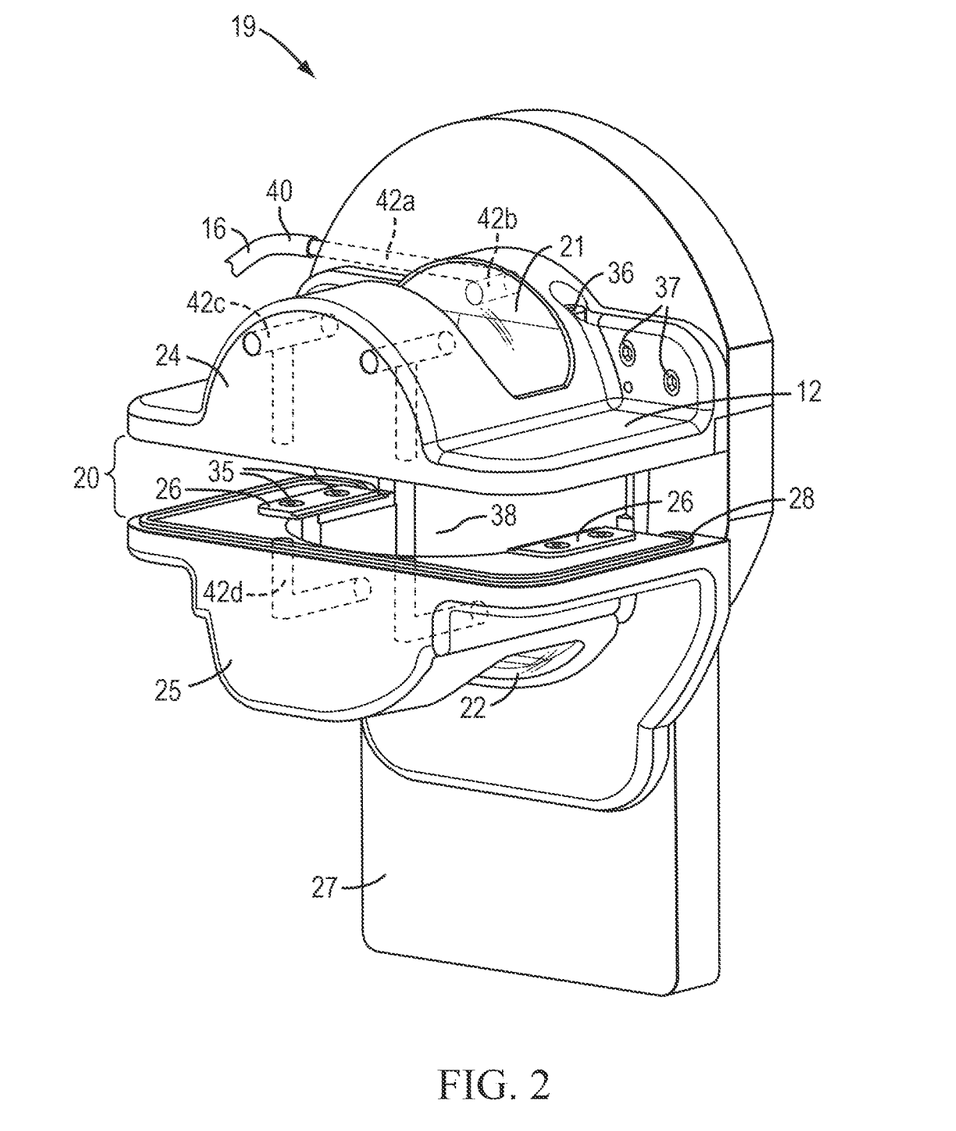
FIG. 2 is a perspective view of an exemplary embodiment of the device for creating a low-background scattering environment of FIG. 1 shown in isolation and in an open position.

FIG. 2 illustrates the device 19 with the housing 12 in an open position. When in the open position, the housing 12 may be configured to provide access to an x-ray diffractometer stage (not depicted in FIG. 2) via the stage access opening 20. In this position, loading of a sample onto the diffractometer stage and into the interior of the housing 12 may occur through the stage access opening 20.

Figure 3:
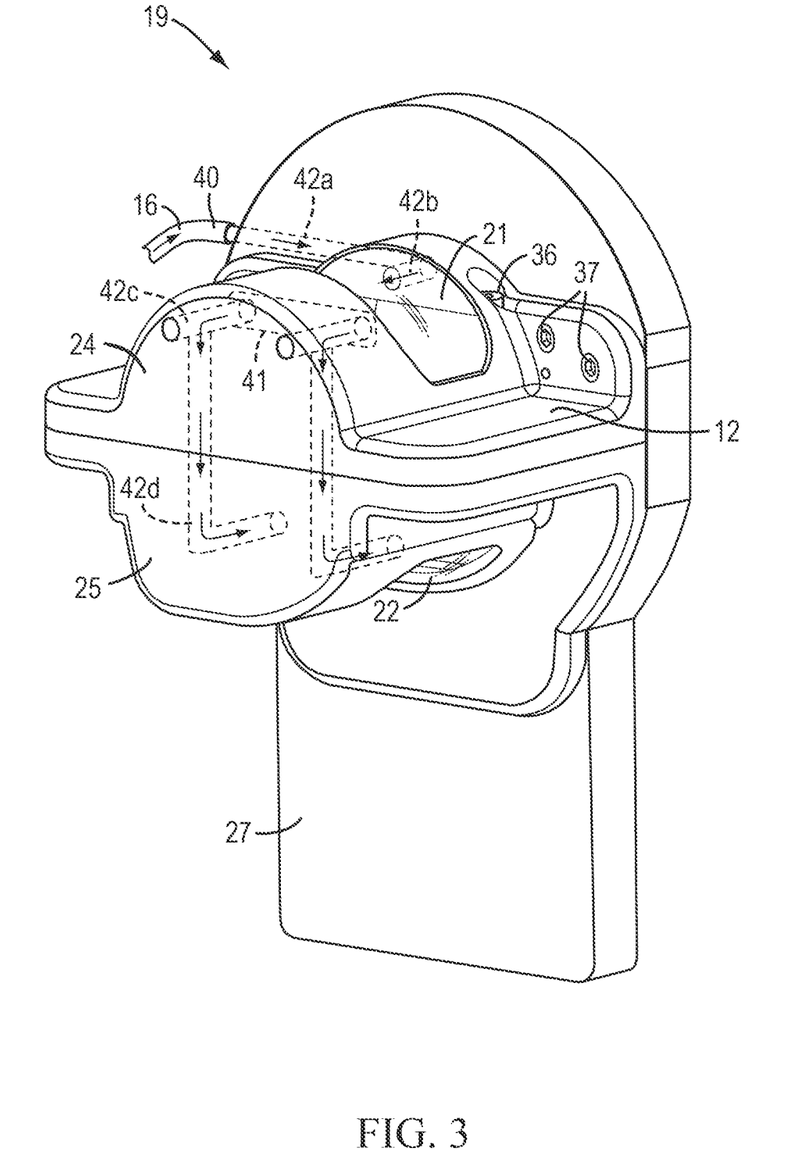
FIG. 3 is a perspective view of an exemplary embodiment of the device of FIG. 2 shown in a closed position.

FIG. 3 illustrates the device 19 with the housing 12 in a closed position. When in the closed position, the housing 12 may be configured to substantially enclose the stage. In the closed position, the housing 12 may define a chamber interior defining a region proximate to the stage that can contain a low-background scattering environment.

Figure 4:
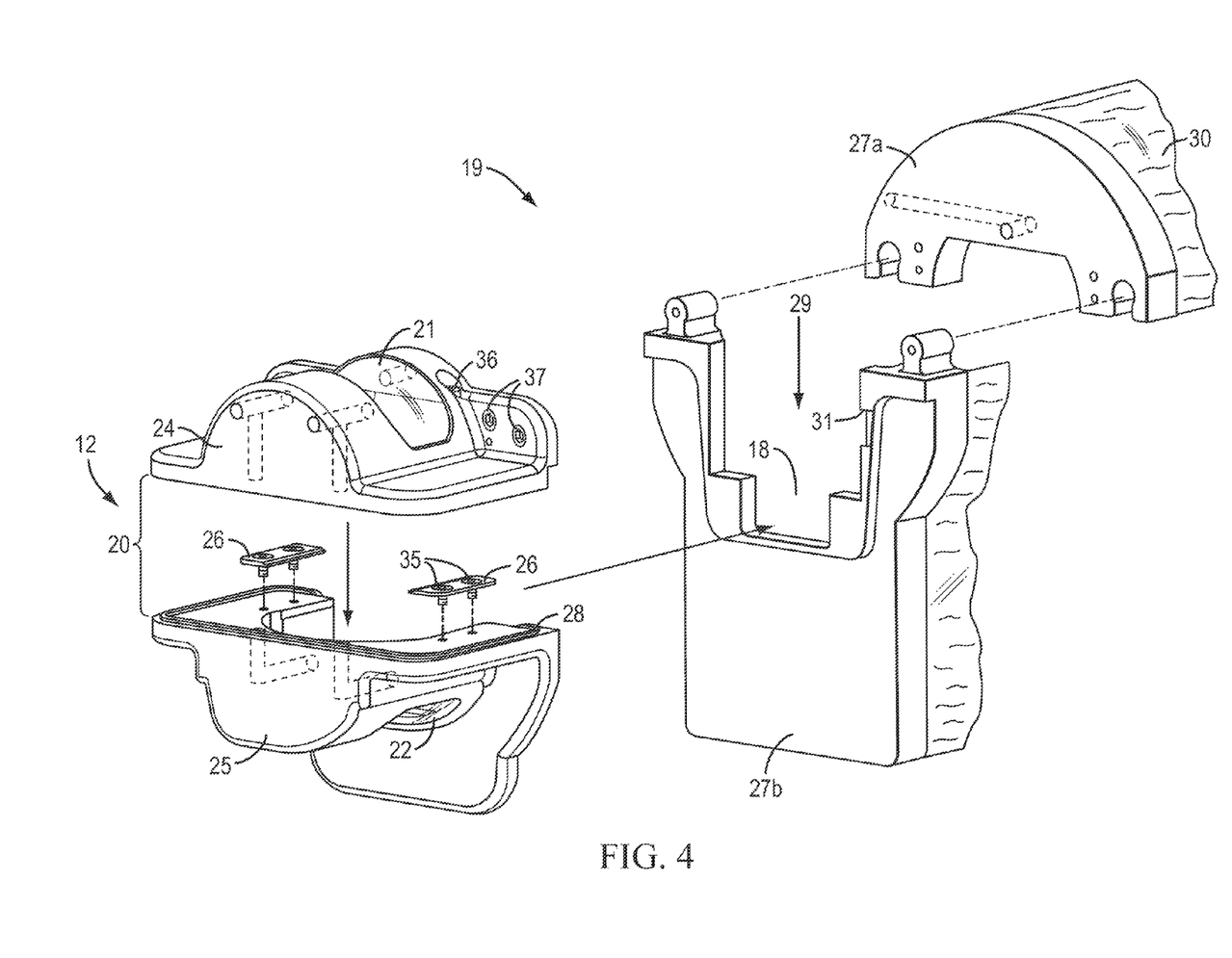
FIG. 4 is an exploded view of an exemplary embodiment of the housing that comprises the device of FIGS. 2 and 3.

FIG. 4 illustrates an exploded, isometric view of an exemplary embodiment of the device 19, including the housing 12 and the backplate 27.

Figure 5:
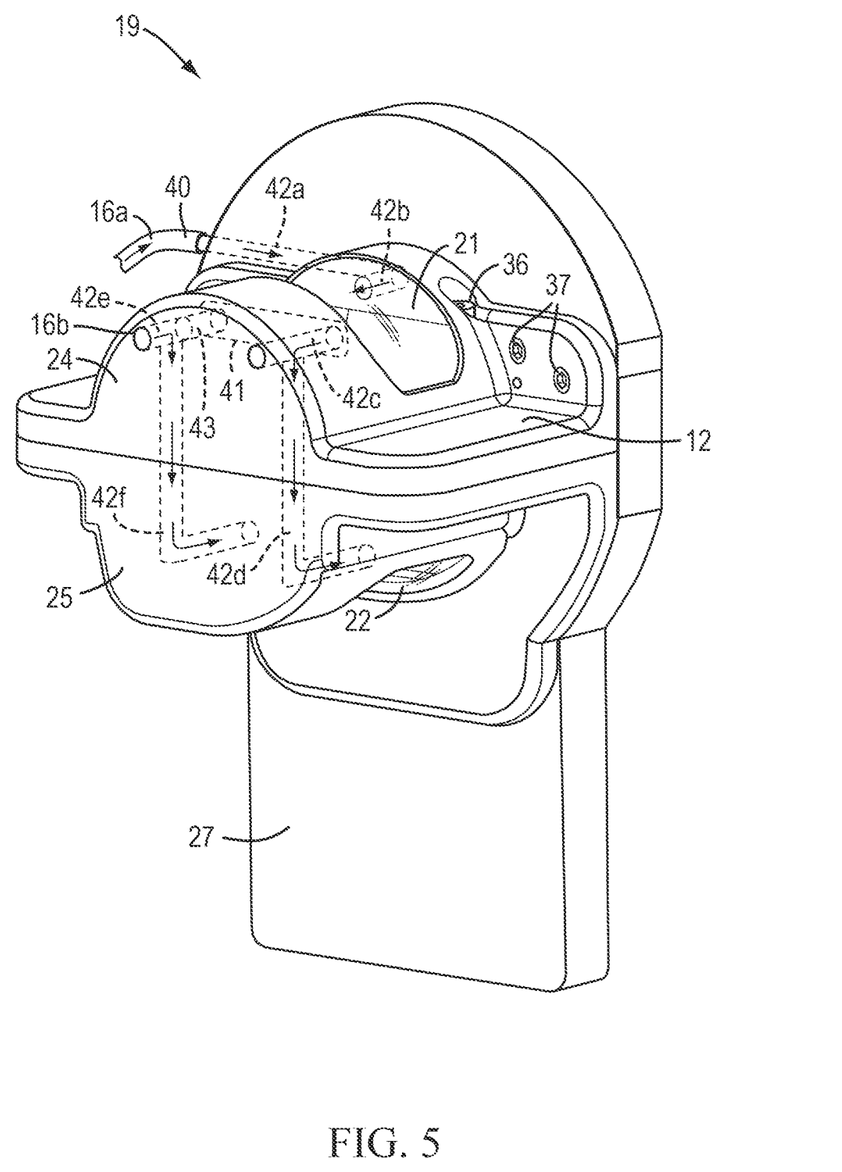
FIG. 5 is a perspective view of another exemplary embodiment of a device for creating a low-background scattering environment shown in isolation and in a closed position.

FIG. 5 illustrates another exemplary embodiment of the device 19 comprising two inlets 16*a*, 16*b* with the housing 12 in a closed position.

Figure 6:
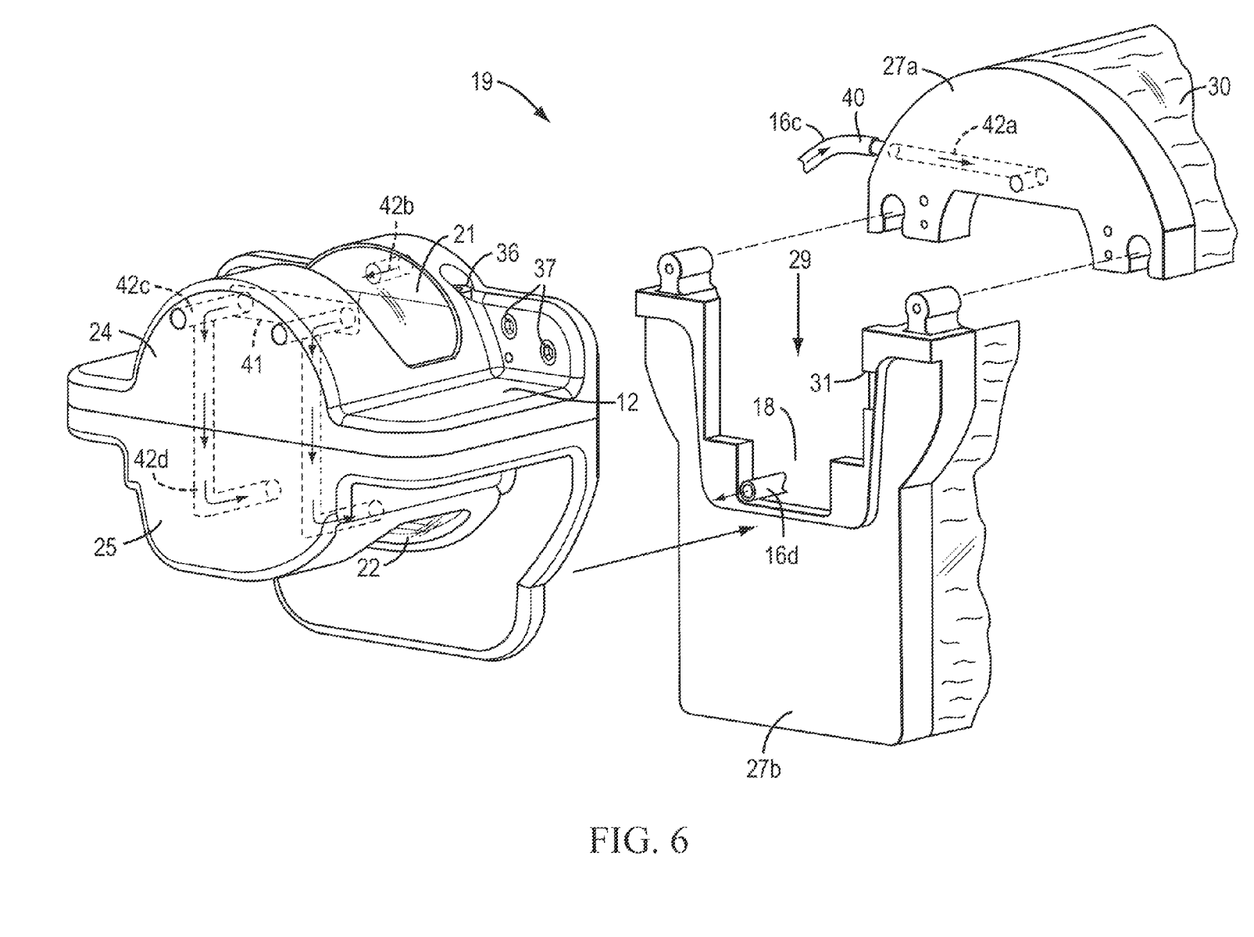
FIG. 6 is a partially exploded view of another exemplary embodiment of a device for creating a low-background scattering environment shown in isolation and in a closed position.

FIG. 6 illustrates a partially exploded, isometric view of another exemplary embodiment of the device 19 comprising two inlets 16*c*, 16*d* with the housing 12 in a closed position.

As depicted in FIGS. 1-6, the housing 12 may comprise windows 21, 22 positioned substantially opposite to one another and configured to transmit x-ray photons therethrough. As FIG. 1 depicts, when in use with an x-ray diffractometer, a window 21 may be positioned between the x-ray source assembly 13 and the stage 11, and the window 22 may be positioned between the stage 11 and the x-ray detector assembly 14 to transmit x-rays from the source 13 through the housing 12 and to the detector 14 when the housing 12 is in the closed position.

In various exemplary embodiments, the windows 21, 22 may be curved, for example, following the contour of a substantially cylindrical surface to accommodate movement or rotation of an x-ray source assembly 13 and/or x-ray detector assembly 14 about the housing 12. The windows 21, 22 may be formed from thin materials that provide relatively weak absorption of x-ray photons. Examples of suitable materials include, but are not limited to, plastics, such as, for example, poly(methyl)methacrylate. In various exemplary embodiments, the materials may have an absorbance coefficient for Cu $K_{alpha}$ ranging from about 5/cm to about 10/cm, such as from about 5.5/cm to about 8.5/cm or, for example, from about 6/cm to about 8/cm. In various exemplary embodiments, thin film windows comprising materials sold under the trade names Etnom® and Mylar® and marketed by Chemplex Industries Incorporated of Palm City, Fla., may be used.

As shown in FIG. 4, the housing 12 of the device 19 may comprise at least a first housing portion 24 and a second housing portion 25. The first housing portion 24 and the second housing portion 25 may be configured to move relative to one another so that in a separated position, the housing 12 is placed in the open position (see FIG. 2), and in a mated position, the housing 12 is placed in the closed position (see FIG. 3).

As explained above with reference to FIG. 1, in various exemplary embodiments, the first and second housing portions 24, 25 may be configured to be coupled to portions of the x-ray diffractometer 15. In an exemplary embodiment, the second housing portion 25 may be configured to be coupled or secured to a stage 11 of the x-ray diffractometer and may be configured to automatically move with the automated motion of at least a portion of the stage. For example, as best shown in FIGS. 2, the second housing portion 25 may define a cut-out opening 38 configured to receive a portion of an x-ray diffractometer stage 11, such as the sample-holding surface 33 of the stage 11 of FIG. 1, and may be secured to the sample-holding surface 33 by a receiving mechanism, such as shims 26 coupled to a surface of the housing 12 and configured to rest on the sample-holding surface 33 of the stage 11. In various embodiments, the receiving mechanism or shims 26 may be fixed to the housing portion 25 by fastening members 35 (see FIG. 7), for example, bolts, screws, etc.

In various exemplary embodiments, as also shown in FIGS. 2-6, the housing 12 of the device 19 may further comprise at least one backplate 27. The at least one backplate 27 may be configured to provide support for the housing 12, couple the housing 12 to an x-ray diffractometer 15, and/or guide movement of one or both housing portions 24, 25.

For example, as shown in FIGS. 1 and 4, the backplate 27 may be secured to the x-ray diffractometer via the first housing portion 24, which may be coupled to the x-ray diffractometer stage 11. As depicted in FIGS. 1 and 4, the backplate 27 may be fixed to the first housing portion 24 by fastening mechanisms 37, which may be selected from bolts, screws, or any other fastening mechanisms. In a further embodiment, the first housing portion 24 may be fixed to the stage by fastening mechanisms 36, such as the screw shown on the upper surface of the first portion 24 in FIG. 4. Although not shown in FIG. 4 due to the perspective, a second fastening mechanism 36 may be on the opposing side of the window 21, as shown in FIG. 1. In the configuration shown in FIG. 1, the first housing portion 24 is coupled to a portion of the stage 11 that remains stationary, such as the stage base 39 (shown in FIG. 7). In such a configuration, the backplate 27 may provide additional support for the first housing portion 24 and guidance for the movement of the second housing portion 25. In additional embodiments, the backplate 27 may be independently secured to the x-ray diffractometer 15. For example, the backplate 27 may encircle a portion of the x-ray diffractometer, such as the stage base 39, and securely rest thereon. Those of ordinary skill in the art will appreciate that the type and arrangement of fastening mechanisms used to secure the backplate and the first housing portion can be selected based on a variety of factors, and the particular configuration shown in FIGS. 1-4 is exemplary and non-limiting.

In further examples, the backplate 27 may also or alternatively provide guidance and support during movement of the second housing portion 25, which may be coupled or secured to the stage 11 of an x-ray diffractometer, and automatically move based on the movement of a portion of the stage, such as the sample-holding surface of the stage 33. In such a configuration, the second housing 25 may slide against the backplate 27 (e.g., up and down) and stop when the housing portion 25 abuts an upper stop surface 31 (shown in FIG. 4) of the backplate 27, thereby assisting in proper mating of the housing portions 24, 25.

In various exemplary embodiments and as depicted in FIG. 4, the at least one backplate 27 may, but is not required to, comprise two portions 27a, 27b. Such structure may facilitate assembly around portions of the x-ray diffractometer 15, such as the diffractometer stage 11, including the stage base 39, the x-ray beam stop (not shown), and/or other optical components. As seen in FIG. 4, the backplate 27 may comprise an opening 29 for receiving portions of the x-ray diffractometer 15.

In various exemplary embodiments, at least one sealing member 28, as best shown in FIGS. 2 and 4, may be disposed so as to seal the first and second housing portions 24, 25, when the housing 12 is in the second position (i.e., when the first and second housing portions 24, 25 are in a mated position). The sealing member 28 may be disposed along a peripheral edge portion of the housing portion 25 where the housing portion 25 mates with the housing portion 24. Although the sealing member 28 is shown in FIGS. 2 and 4 as being disposed on the housing portion 25, those of ordinary skill in the art would appreciate that the sealing member 28 could be disposed on the housing portion 24 instead. In various embodiments, the sealing member 28 may further be disposed so as to seal at least one of the housing portions 24, 25 and the backplate 27. For example, although not shown in the figures, the sealing member 28 may be disposed along the peripheral edge portion of the housing portion, 25 wherein the housing portion 25 mates with the backplate 27. The sealing member 28 may be made of a variety of materials, such as, for example, aluminum, steel, rubber, plastic and/or other synthetic material configured to provide substantially air-tight mating of the housing portions 24, 25 to one another. It is within the ability of one skilled in the art to select the appropriate material for the sealing member 28.

The housing 12 may further comprise one or more additional sealing members, such as the sealing member 30 shown in FIG. 4, configured to provide a seal between the housing 12 and the x-ray diffractometer body 23, as best depicted in FIG. 1. The additional sealing member 30 may prevent leakage, e.g., of the incoming flow of gas through inlet 16, from the housing enclosure in a direction toward the x-ray diffractometer body and away from the sample on the stage, and/or may prevent inflow of air from the surrounding atmosphere, either of which would compromise the low-background scattering environment. For example, in FIG. 1, the additional sealing member 30 is configured to seal the backplate 27 and the x-ray diffractometer body 23 at their opposing surfaces. The additional sealing members 30 may be formed from various materials, including, for example, aluminum, steel, rubber, plastic and/or another synthetic material.

As discussed above with respect to FIG. 1, in various embodiments, the gas flow system of the device 19 or system 10 may comprise at least one inlet 16 configured to be in flow communication with a gas source 17. In other exemplary embodiments, the gas flow system of the device 19 or system 10 may comprise more than one inlet, such as, for example, two inlets 16a, 16b configured to be in flow communication with a gas source 17, as shown in the exemplary embodiment of FIG. 5. As best shown in FIGS. 1 and 3, the at least one inlet 16 may be disposed so as to introduce gas into the housing 12 at a location above a sample (not shown in the figures) on the x-ray diffractometer stage 11. It is within the ability of one ordinarily skilled in the art to determine the type of gas source appropriate for achieving a low-background scattering environment. For example, in at least one embodiment, the gas source may be helium.

As depicted in FIGS. 3, 5 and 6, the gas flow system of the device or system may further comprise a flow distributor 41, such as, for example, a diffuser in flow communication with the at least one inlet. It is within the ability of one skilled in the art to select a flow distributor for use in the device to direct the flow or alter the distribution of the gas from the gas source into and/or throughout the housing as desired during introduction of the gas into the housing. In FIGS. 3, 5 and 6, the flow distributor 41 directs the flow of the gas after it has passed into the upper housing portion 24.

As also discussed above, in various embodiments, the gas flow system of the device 19 or system 10 may comprise at least one outlet configured to vent or flow gas out of the housing 12 and the device 19. The at least one outlet may be disposed so as to flow or vent gas out from a location below the x-ray diffractometer stage 11. As best shown in FIG. 4, one outlet may be formed by an opening 18 in the backplate portion 27b configured to receive portions of the x-ray diffractometer and also to permit gas to leak from the housing 12 and out portions of the opening 18 that do not form a sealed mating engagement with portions of the x-ray diffractometer. In other embodiments (not shown), the outlet may be a mechanism or flow-regulating device.

It is within the ability of one ordinarily skilled in the art to determine a configuration to allow flow of gas out of the housing. In at least one embodiment, the outlet may be configured to vent gas, such as air or helium, from the housing into the atmosphere. In another embodiment, the outlet may be a more defined outlet structure (e.g., similar to inlet 16) in flow communication with a vacuum (not shown) and configured to create a low-pressure environment in the housing.

In further embodiments, the gas flow system 40 may comprise flow paths 42 permitting flow through the housing to one or more portions of the device. For example, as depicted in FIG. 2, the at least one inlet 16 may be configured to flow gas into the backplate 27, and the backplate 27 and/or first housing portion 24 may comprise flow paths 42a, 42b configured to flow gas through their thicknesses to the housing enclosure over the sample, as shown by the dotted lines in FIG. 3. Similarly, the first and/or second housing portions 24, may comprise flow paths 42c, 42d configured to flow gas through their thickness to the housing chamber at a location under the stage 11 and/or out the at least one outlet 18. The arrows shown in FIG. 3 represent an exemplary flow path for the gas. When either the inlet or outlet are configured to flow gas through the backplate or other portion of the housing, the inlet and/or outlet penetrates through the thickness of the backplate 27 and/or housing 12 to permit gas to enter and/or exit the chamber of the housing in the closed position. The various flow passages may be defined by the housing and backplate structures themselves or may comprise separate manifolds in connection with the housing and backplate.

As depicted in FIGS. 5 and 6, for example, in various additional embodiments, the device 19 may comprise two inlets. A first inlet may be disposed so as to introduce gas into the housing 12 at a location above a sample on the x-ray diffractometer stage 11, and a second inlet may be disposed so as to introduce gas into the housing 12 at a location below the stage 11. While not wishing to be bound by a particular theory, the inventors believe that the addition of a second inlet may improve the performance of the device 19 by providing an additional means of filling the second housing portion 25.

As shown in FIG. 5, similar to the above embodiment of FIG. 3, a first inlet 16a may be disposed within a side portion of backplate 27 and configured to flow gas into the backplate 27. The backplate 27 and/or first housing portion 24 may comprise flow paths 42a, 42b configured to flow gas through their thicknesses to the housing enclosure over the sample, as shown by the dotted lines in FIGS. 5. Similarly, the first and/or second housing portions 24, 25 may comprise flow paths 42c, 42d configured to flow gas through their thickness to the housing chamber at a location under the stage 11 and/or out the at least one outlet 18. A second inlet 16b may be disposed within a front face of the first housing portion 24 and configured to flow gas directly into the first housing portion 24. The first and/or second housing portions 24, 25 may comprise flow paths 42e, 42f configured to flow gas through their thickness to the housing chamber at a location under the stage 11 and/or out the at least one outlet 18. As shown in FIG. 5, the flow path 42e may be plugged, for example, by a plug 43 configured to direct gas flow through the flow path 42f to fill the lower housing potion 25. In various embodiments, for example, the flow path 42e may be plugged with a clay plug 43. The arrows shown in FIG. 5 represent exemplary flow paths for the gas.

As shown in FIG. 6, in various further embodiments, the device 19 may comprise inlets 16c, 16d. As above, a first inlet 16c may be disposed within a side portion of backplate 27 and may be configured to flow gas into the backplate 27. The backplate 27 and/or first housing portion 24 may comprise flow paths 42a, 42b configured to flow gas through their thicknesses to the housing enclosure over the sample, as shown by the dotted lines in FIGS. 6. Similarly, the first and/or second housing portions 24, 25 may comprise flow paths 42c, 42d configured to flow gas through their thickness to the housing chamber at a location under the stage 11 and/or out the at least one outlet 18. A second inlet 16d (e.g. a flexible tube) may be disposed within the outlet 18 and configured to flow gas into the housing chamber at a location under the stage 11 and back out the outlet 18.

Those of ordinary skill in the art would understand that the embodiments depicted in FIGS. 5 and 6 are exemplary only, and that the device 19 may comprise any number of inlets and outlets in various locations. It is within the ability of one ordinarily skilled in the art to determine the appropriate number and/or location of the inlets and outlets to ensure adequate gas flow both above and below the stage 11 of the device 19.

Figure 7:
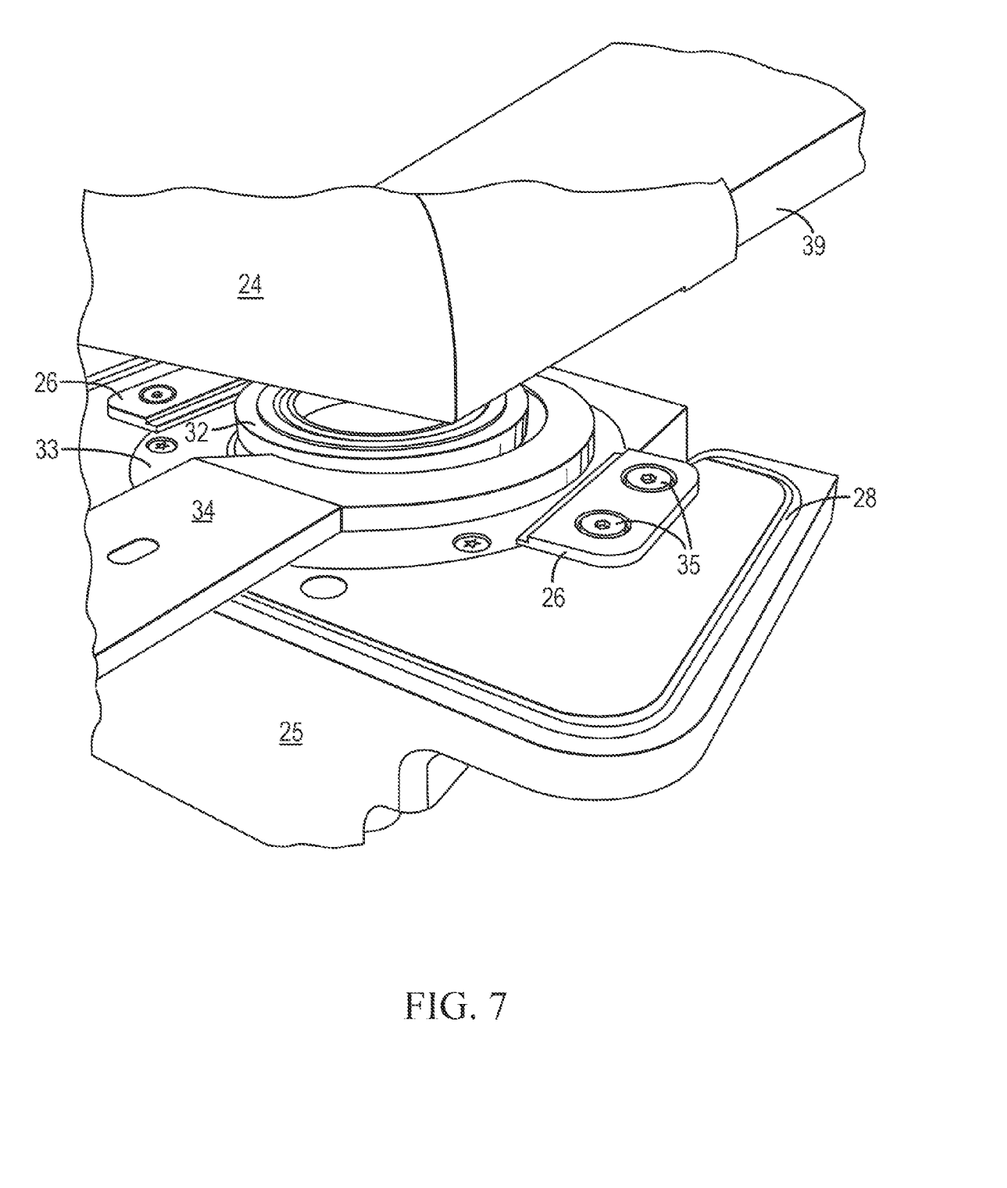
FIG. 7 is a partial perspective view of the exemplary system of FIG. 1 and a sample loading mechanism loading a sample onto the x-ray diffractometer stage.

FIG. 7 illustrates a partial view of the housing 12 and stage 11 with the housing 12 in an open position. In the open position, the stage 11 may be in position to allow loading of a sample 32 to the stage 11. Likewise, the housing 12 may be configured to provide access to the stage 11 via the stage access opening 33.

In various embodiments, the x-ray diffractometer system 10 may further comprise an automated sample loading mechanism 34. For example, in at least one embodiment, the automated sample loading mechanism 34 may comprise a robotic arm, as depicted in FIG. 7. In various embodiments, the sample loading mechanism 34 may operate by setting a sample 32 on the stage 11 by lowering it from a position above the stage 11 in the orientation of FIG. 7. The sample may be removed from the stage 11 after analysis by lifting the sample 32 from the sample-holding surface 33 of the stage 11. Those having ordinary skill in the art are familiar with various x-ray diffractometers that utilize such automated sample loading mechanisms to load sample onto a stage, and a variety of configurations may be used in accordance with the present teachings to load the sample onto an x-ray diffractometer stage 11 via the sample access opening 20 of the housing 12.

Exemplary embodiments of the disclosure also contemplate methods for collecting x-ray diffraction data from a sample, for example, using the system 10 and devices 19 of FIGS. 1-6. The method may comprise automatically moving a housing 12 to the open position wherein the housing is configured to provide access to an x-ray diffractometer stage 11, as shown in FIG. 7. The housing 12 used in the method may exist in various embodiments as described with respect to the housing of the systems and devices also disclosed herein.

The method further comprises loading at least one sample 32 onto the x-ray diffractometer stage 11. In various embodiments of the method, the loading of the x-ray diffractometer stage may be automated, such as using the robotic arm 34 in FIG. 7. In additional embodiments of the disclosure, the sample may be a powder of any composition, for instance a pharmaceutical compound.

The method further comprises automatically moving the housing 12 to the closed position, wherein the housing is configured to substantially enclose the x-ray diffractometer stage 11 for creating a low-background scattering environment proximate to the stage. In various embodiments of the method, the housing 12 may be coupled or secured to the stage, 11 and automatically moving the housing 12 may comprise moving at least a portion of the stage 11. In at least one embodiment of the disclosure, the housing 12 used in said method may further comprise a first housing portion 24 and a second housing portion 25, one of the first and second housing portions 24, 25 may be coupled or secured to the stage 11, and automatically moving the housing 12 may comprise moving a portion of the stage 11.

The method further comprises flowing gas out of the interior of the housing 12 in the closed position to create a low-background scattering environment proximate to the stage 11. In various embodiments of the disclosed method, flowing gas out of the housing 12 may comprise venting gas from at least one outlet formed by opening 18 (shown in FIG. 4). In additional embodiments, the method may further comprise flowing gas, such as helium, into the housing 12, and in various embodiments, the gas may flow through a flow distributor 41 (shown in FIGS. 3, 5 and 6) or, for example, through a diffuser (not shown). For example, in at least one embodiment, helium may flow from a gas source 17 into the housing 12 from a location above the sample, thereby forcing air and excess helium to below the sample and through the vent outlet formed by opening 18.

Referring to FIG. 1, the method additionally comprises transmitting x-ray photons into the housing 12 from an x-ray source assembly 13 and detecting the diffracted x-ray photons from the sample 32 (not shown) loaded on the stage 11 on the x-ray detector assembly 14.

In further embodiments, the method may be automatically repeated at least once, for example, at least two times, at least ten times, at least fifteen times, or over fifty times, thereby automatically analyzing multiple samples.

The disclosure also relates to methods for reducing background scattering due to the environment in x-ray diffraction data, comprising collecting x-ray diffraction using the method described herein.

The various systems and devices disclosed herein may be useful in collecting x-ray diffraction data for identification and/or characterization of samples, including solids (such as powders), liquids or liquid suspensions, and particularly for active pharmaceutical ingredients and pharmaceutical mixtures and formulations.

EXAMPLES

As discussed above, the disclosure contemplates devices for creating a low-background scattering environment around a stage of an x-ray diffractometer. To verify the effectiveness of the devices, systems and methods in accordance with exemplary embodiments of the teachings, various laboratory tests were conducted with and without a low-background scattering environment, as achieved by the disclosed devices, systems and methods, around the stage of an x-ray diffractometer.

A device in accordance with the disclosure, and as depicted in FIG. 1, was utilized in the collection of x-ray diffraction data. Specifically, in Examples 1 and 2 below, a PANalytical B.V. X'Pert PRO MPD diffractometer was modified as described above to include a device to create a helium environment in a region proximate to, and substantially surrounding, the stage. In both Examples, the device comprised a housing comprising a first housing portion and a second housing portion. The first housing portion was coupled with a backplate to a stationary portion of the x-ray diffractometer stage, and the second housing was coupled to a portion of the x-ray diffractometer stage that moved automatically. In Example 1, one inlet on the upper portion of the backplate allowed helium to flow into the housing enclosure from above the sample and stage, using the embodiment of the device shown in FIGS. 2 and 3. An outlet on the second housing portion allowed air and helium to vent out of the housing.

In Example 2, two inlets (one inlet on the upper portion of the backplate and one inlet on the first housing portion) allowed helium to flow into the housing enclosure from above the sample and stage, using the embodiment of the device shown in FIG. 5. An outlet on the second housing portion allowed air and helium to vent out of the housing.

In each of Examples 1 and 2, the system and device were configured to transmit x-ray photons from the x-ray source assembly through a window on the first housing portion, through a window on the second housing portion, and to an x-ray detector assembly for collection.

X-ray powder diffraction patterns were collected for the Examples with a PANalytical B.V. X'Pert PRO MPD diffractometer using an incident beam of Cu radiation produced using an Optix long, fine-focus source. An elliptically graded multilayer mirror was used to focus Cu K$_{alpha}$ X-rays through the specimen and onto the detector. A specimen of the sample was sandwiched between 3 μm-thick polymeric films and analyzed in transmission geometry. A beam-stop and a helium atmosphere were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

Example 1

Blank patterns were collected using a one-half degree divergence slit, a one-quarter degree anti-scatter slit, and 0.04 rad soller slits. The detector was scanned at 1.5 degree 2θ per minute with a 0.050 degree 2θ step size. The x-ray generator used 45 kV and 40 mA current.

First, x-ray diffraction data were collected without flowing helium into the housing (in a second or closed position) via the single inlet and with an empty sample holder on the stage. The resulting x-ray diffraction pattern is shown in FIG. 8.

Next, x-ray diffraction data were collected after flowing helium into the housing (in a second or closed position) and with the same empty sample holder on the stage. The resulting x-ray diffraction pattern is also shown in FIG. 8.

Figure 8:
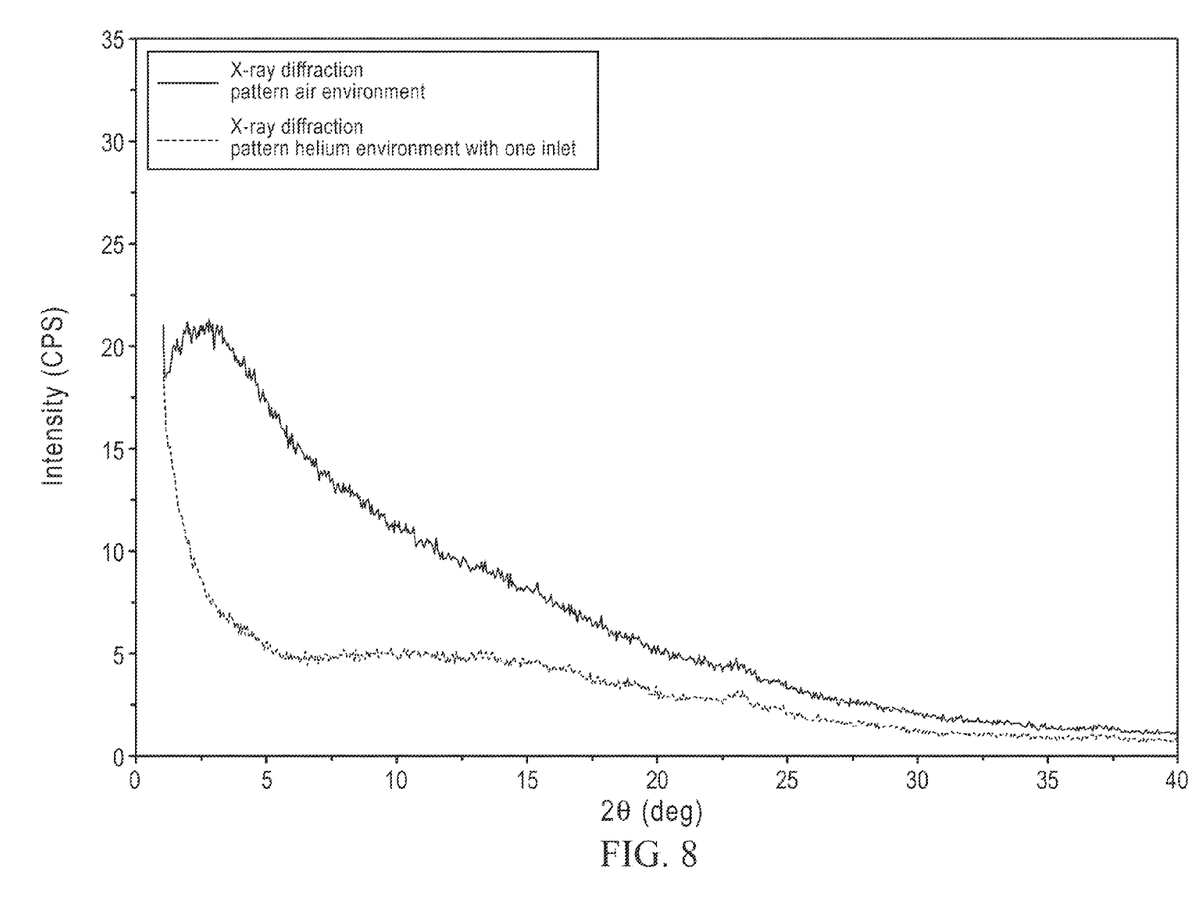
FIG. 8 is a comparison of x-ray diffraction patterns of an empty sample holder obtained in accordance with the procedure set forth in Example 1, using a device of the embodiment of FIG. 3, with an air environment and with helium gas, respectively, proximate to the stage.

As can be seen by comparing the diffraction patterns of FIG. 8, the background scattering is reduced in a low-background scattering environment such as helium.

Example 2

Stearic acid patterns were collected using a one-half degree divergence slit, a beam knife, and 0.02 rad soller slits. The detector was scanned at 1.0 degree 2θ per minute with a 0.017 degree 2θ step size. The x-ray generator used 45 kV and 40 mA current.

First, x-ray diffraction data were collected without flowing helium into the housing (in a second or closed position) and with a sample holder containing a stearic acid specimen on the stage. The resulting x-ray diffraction pattern is shown in FIG. 9.

Next, x-ray diffraction data were collected after flowing helium into the housing (in a second or closed position) via the two inlets and with the same specimen on the stage. The resulting x-ray diffraction pattern is also shown in FIG. 9.

Figure 9:
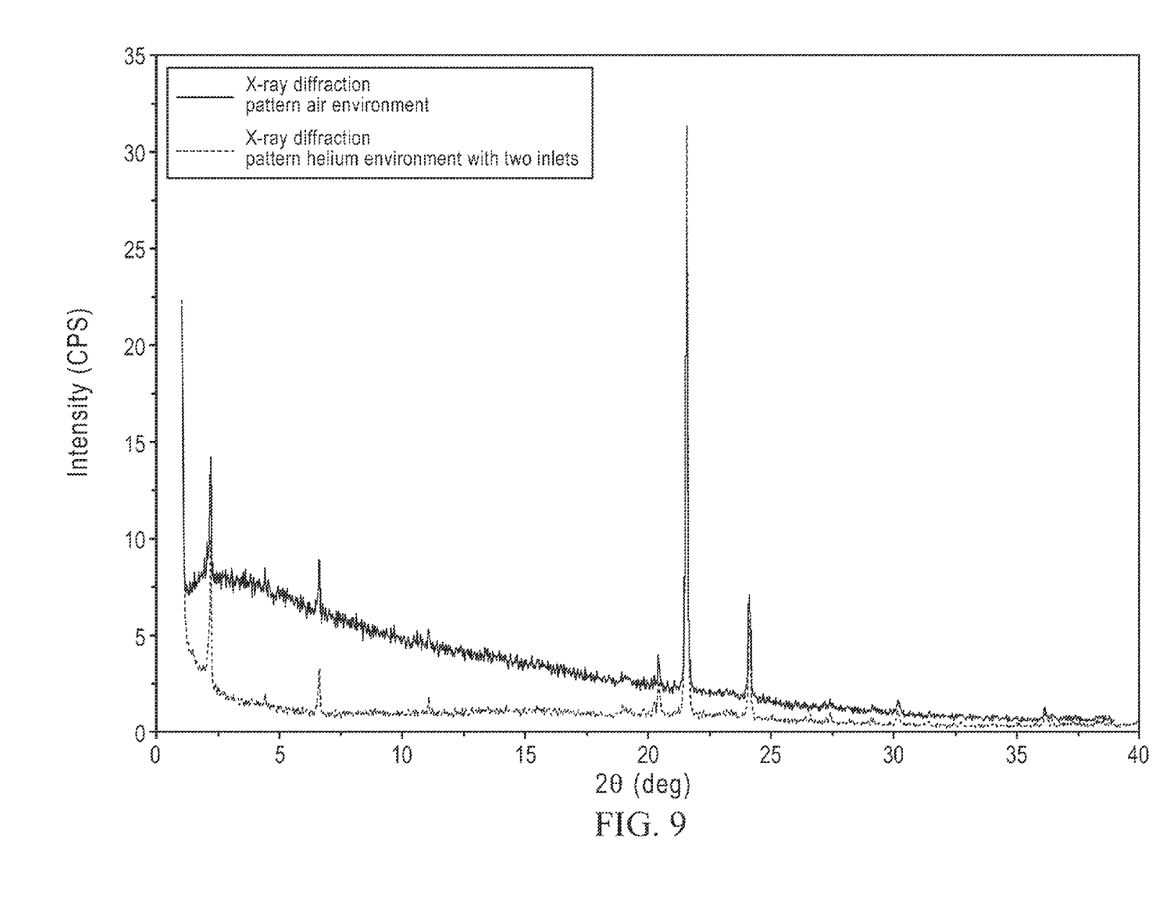
FIG. 9 is a comparison of x-ray diffraction patterns of Stearic acid obtained in accordance with the procedure set forth in Example 1, using a device of the embodiment of FIG. 5 with an air environment and with helium gas, respectively, proximate to the sample.

As can be seen by comparing the diffraction patterns of FIG. 9, the background scattering is reduced in a low-background scattering environment such as helium. The background scattering reduction permits resolution of XRPD peaks that are obscured by noise in the pattern collected in an air environment.

Various exemplary embodiments of the devices, systems, and methods of the disclosure may provide the additional advantages of cost effectiveness and safety by limiting the volume of the low-background scattering environment produced around the x-ray diffractometer stage.

Moreover, the automated nature of the devices, systems, and methods of the disclosure and their ability to achieve a low-background scattering environment quickly, may also be utilized for high-throughput analysis of samples. For example, in various embodiments, a low-background scattering environment comprising helium in a housing may achieve equilibrium in less than one minute, for example, less than 30 seconds.

Unless otherwise indicated, all numbers used in the specification and claims are to be understood as being modified in all instances by the term "about," whether or not so stated. It should also be understood that the precise numerical values used in the specification and claims form additional embodiments of the invention. Efforts have been made to ensure the accuracy of the numerical values disclosed herein. Any measured numerical value, however, can inherently contain certain errors resulting from the standard deviation found in its respective measuring technique.

As used herein, the use of "the," "a," or "an" means "at least one," and should not be limited to "only one" unless explicitly indicated to the contrary. Thus, for example, the use of "the inlet" or "inlet" is intended to mean at least one inlet.

Other embodiments will be apparent to those skilled in the art from consideration of the specification and practice of the invention disclosed herein. It is intended that the specification and examples be considered as exemplary only, and the claims be given their broadest scope including equivalents.

What is claimed is:

1. A device for creating a gaseous environment proximate to an x-ray diffractometer stage, the device comprising:
a housing configured to move in an automated manner to at least a first position and a second position, wherein the housing in the first position is configured to provide access to the stage to load the stage with a sample and wherein the housing in the second position is configured to substantially enclose the stage; and
a gas flow system in flow communication with the housing and configured to flow air out of the housing to create a low-background scattering environment proximate to the stage when the housing is in the second position;
wherein the housing in the second position is configured to transmit x-ray photons from an x-ray source assembly to an x-ray detector assembly of the x-ray diffractometer.

2. The device of claim 1, wherein said housing comprises at least a first housing portion and a second housing portion.

3. The device of claim 2, wherein one of the first and second housing portions is configured to be coupled to a portion of the x-ray diffractometer body.

4. The device of claim 2, wherein one of the first and second housing portions is configured to be coupled to the stage.

5. The device of claim 2, wherein the first housing portion and the second housing portion are configured to be coupled to the x-ray diffractometer stage.

6. The device of claim 5, wherein at least one of the first housing portion and second housing portion is configured to automatically move based on movement of the stage.

7. The device of claim 1, wherein the housing is configured to move based on movement of the stage.

8. The device of claim 2, further comprising at least one sealing member configured to seal the first and second housing portions when the housing is in the second position.

9. The device of claim 1, further comprising at least one additional sealing member configured to seal the housing and a portion of the x-ray diffractometer body when the housing is in the second position.

10. The device of claim 1, wherein the gas flow system comprises at least one inlet.

11. The device of claim 10, wherein the gas flow system comprises two inlets.

12. The device of claim 11, wherein the gas flow system comprises a first inlet disposed so as to introduce gas into the housing at a location above the sample on the stage, and a second inlet disposed so as to introduce gas into the housing at a location below the stage.

13. The device of claim 10, further comprising a flow distributor in flow communication with the at least one inlet.

14. The device of claim 1, wherein the at least one inlet is disposed so as to introduce gas into the housing at a location above a sample on the stage.

15. The device of claim 1, wherein the gas flow system comprises at least one outlet.

16. The device of claim 15, wherein the at least one outlet is positioned to permit gas to flow out of the housing at a location below the stage.

17. A method for collecting x-ray diffraction data from a sample, said method comprising:
automatically moving a housing to a first position wherein the housing is configured to provide access to an x-ray diffractometer stage;
loading a sample onto the x-ray diffractometer stage;
automatically moving the housing to a second position wherein the housing is configured to substantially enclose the x-ray diffractometer stage for creating a low-background scattering environment proximate to the stage;
flowing gas out of the housing in the second position to create a low-background scattering environment proximate to the stage;
transmitting x-ray photons into the housing; and
detecting x-ray photons diffracted from the sample loaded on the stage.

18. The method of claim 17, wherein loading the x-ray diffractometer stage is automated.

19. The method of claim 18, wherein the method is automatically repeated at least once.

20. The method of claim 17, wherein said housing further comprises a first housing portion and a second housing portion, at least one of the first and second housing portions is coupled to the stage, and automatically moving the housing comprises moving a portion of the stage.

21. The method of claim 17, wherein the housing is coupled to the stage, and automatically moving the housing comprises moving the stage.

22. The method of claim 17, wherein flowing gas out of the housing in the second position to create a low-background scattering environment proximate to the stage comprises flowing gas from a location above a sample on the stage to a location below the sample.

23. The method of claim 22, further comprising flowing gas through a flow distributor before flowing gas from a location above the sample on the stage to a location below the sample.

24. The method of claim 17, wherein the sample comprises a pharmaceutical compound.

25. An x-ray diffractometer system comprising:
   a stage configured to receive a sample to be analyzed;
   a housing configured to move in an automated manner to at least a first position and a second position, wherein the housing in the first position is configured to provide access to the stage to load the stage with a sample, and wherein the housing in the second position is configured to substantially enclose the stage and to transmit x-ray photons from an x-ray source assembly to an x-ray detector assembly of the x-ray diffractometer; and
   a gas flow system in flow communication with the housing and configured to flow air out of the housing to create a low-background scattering environment proximate to the stage when the housing is in the second position.

26. The x-ray diffractometer system of claim 25, further comprising an automated sample loading mechanism.

27. The x-ray diffractometer system of claim 25, wherein said housing further comprises a first housing portion and a second housing portion.

28. The x-ray diffractometer system of claim 27, wherein the housing comprises a first housing portion and a second housing portion, and at least one of the first and second housing portions is configured to be coupled to the stage.

\* \* \* \* \*